US012792132B2

(12) United States Patent
McLeod et al.

(10) Patent No.: US 12,792,132 B2
(45) Date of Patent: Nov. 10, 2026

(54) FORCE-BASED CONTROL OF A VIRTUAL OBJECT BEING DISPLAYED BY A COMPUTER-ASSISTED MEDICAL SYSTEM

(71) Applicant: Intuitive Surgical Operations, Inc., Sunnyvale, CA (US)

(72) Inventors: A Jonathan McLeod, Sunnyvale, CA (US); Azad Shademan, Campbell, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 270 days.

(21) Appl. No.: 18/703,920

(22) PCT Filed: Dec. 15, 2022

(86) PCT No.: PCT/US2022/053055

§ 371 (c)(1),
(2) Date: Apr. 23, 2024

(87) PCT Pub. No.: WO2023/114427

PCT Pub. Date: Jun. 22, 2023

(65) Prior Publication Data

US 2026/0169548 A1 Jun. 18, 2026

Related U.S. Application Data

(60) Provisional application No. 63/290,867, filed on Dec. 17, 2021.

(51) Int. Cl.

*G06F 3/01* (2006.01)
*A61B 34/00* (2016.01)
(Continued)

(52) U.S. Cl.

CPC .............. *G06F 3/011* (2013.01); *A61B 34/35* (2016.02); *A61B 34/77* (2016.02); *G06T 19/20* (2013.01);
(Continued)

(58) Field of Classification Search

CPC ........ G06F 3/011; G06F 3/0338; G06F 3/038; G06F 3/033; A61B 34/35; A61B 34/77;
(Continued)

(56) References Cited

U.S. PATENT DOCUMENTS

2003/0193475 A1 10/2003 Rosenberg et al.
2017/0071681 A1* 3/2017 Peine ..................... A61B 34/74
(Continued)

FOREIGN PATENT DOCUMENTS

WO WO-2021167954 A1 8/2021

OTHER PUBLICATIONS

International Search Report and Written Opinion for Application No. PCT/US2022/053055, mailed Mar. 29, 2023, 13 pages.
(Continued)

*Primary Examiner* — Brent D Castiaux

(57) ABSTRACT

An illustrative virtual image processing system may be configured to constrain a degree of freedom associated with movement of a user input device, detect a user force applied to the user input device in the degree of freedom, and manipulate, based on the user force, a pose of a virtual object being displayed by a display device.

20 Claims, 11 Drawing Sheets

(51) Int. Cl.
*A61B 34/35* (2016.01)
*G06T 19/20* (2011.01)

(52) U.S. Cl.
CPC ...... *G06T 2200/24* (2013.01); *G06T 2210/41* (2013.01); *G06T 2219/2016* (2013.01)

(58) Field of Classification Search
CPC ... A61B 34/74; A61B 90/03; A61B 2034/105; A61B 2034/2059; A61B 2034/2065; G06T 19/20; G06T 2200/24; G06T 2210/41; G06T 2219/2016
See application file for complete search history.

(56) References Cited

U.S. PATENT DOCUMENTS

2021/0137624 A1* 5/2021 Maret .................... A61B 34/74
2021/0158622 A1* 5/2021 Leelaphattarakij .......................... G06F 3/04815

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2022/053055, mailed Jun. 27, 2024, 10 pages.

* cited by examiner

FORCE-BASED CONTROL OF A VIRTUAL OBJECT BEING DISPLAYED BY A COMPUTER-ASSISTED MEDICAL SYSTEM

RELATED APPLICATIONS

The present application is a U.S. National Stage Application under 35 U.S.C. § 371 of International Application No. PCT/US2022/053055, filed Dec. 15, 2022, which claims priority to U.S. Provisional Patent Application No. 63/290,867, filed Dec. 17, 2021, each of which is hereby incorporated by reference in its entirety.

BACKGROUND INFORMATION

A system used during a medical procedure may present a virtual object in an image being displayed by a display device. For example, the system may present a three-dimensional (3D) preoperative model within an image of patient anatomy as captured by an endoscope.

In some instances, it may be desirable to adjust a pose (e.g., a position and/or orientation) of the virtual object being displayed in the image. For example, it may be desirable for a user to adjust a pose of a 3D preoperative model to align the 3D preoperative model with patient anatomy depicted within the image.

In some scenarios, it may be desirable for a user to adjust the pose of the virtual object by moving (e.g., rotating and/or translating) the same user input device that is also used to control one or more instruments attached to one or more manipulator arms of a computer-assisted medical system. Unfortunately, adjustments of the pose of the virtual object may need to be separated into several smaller steps due to a limited range of motion in movement of the user (e.g., a limited range of motion in movement at a wrist of a user). The movement of the user input device may further cause a disconnect between the user input device and an instrument controlled by the user input device once the user has completed adjusting the pose of the virtual object and resumes using the user input device to control an instrument.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An illustrative system includes a memory storing instructions and a processor communicatively coupled to the memory and configured to execute the instructions to: constrain a degree of freedom associated with movement of a user input device; detect a user force applied to the user input device in the degree of freedom; and manipulate, based on the user force, a pose of a virtual object being displayed by a display device.

An illustrative system includes a user input device; a display device configured to display a virtual object; and a control system communicatively coupled with the user input device and the display device, wherein the control is configured to: constrain a degree of freedom associated movement of the user input device, detect a user force applied to the user input device in the degree of freedom, and manipulate, based on the user force, a pose of the virtual object being displayed by the display device.

An illustrative method includes constraining a degree of freedom associated with movement of a user input device; detecting a user force applied to the user input device in the degree of freedom; and manipulating, based on the user force, a pose of a virtual object being displayed by a display device.

An illustrative non-transitory computer-readable medium may store instructions that, when executed, direct a processor of a computing device to: constrain a degree of freedom associated with movement of a user input device; detect a user force applied to the user input device in a direction associated with the degree of freedom; and manipulate, based on the user force, a pose of a virtual object being displayed by a display device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

An illustrative virtual image processing system may be configured to manipulate a pose of a virtual object being displayed by a display device based on a user force that a user applies to a user input device in addition to or instead of movement of the user input device.

For example, the virtual image processing system may be configured to constrain a degree of freedom associated with the user input device, detect a user force applied to the user input device in the degree of freedom, and manipulate, based on the user force, the pose of the virtual object being displayed by the display device. The virtual image processing system may further be configured to detect a termination of the user force to the user input device, and abstain from manipulating, based on the termination of the user force, the pose of the virtual object being displayed by the display device.

As another example, the virtual image processing system may be configured to detect the user force to the user input device based on movement of the user input device away from one or both of an initial spatial position or an initial spatial orientation of the user input device. In instances where the user force causes the user input device to move, the constrained degree of freedom may cause the user input device to move towards one or both of the initial spatial position or the initial spatial orientation, without affecting the pose of the virtual object, when the user force is no longer being applied to the user input device. This may cause the user input device to return towards its initial position and/or orientation after the user stops applying the user force without affecting the pose of the previously manipulated virtual object.

The principles described herein may result in improved virtual object manipulation compared to conventional techniques that are not based on a user force being applied to a user input device, as well as provide other benefits as described herein. For example, manipulating a pose of a virtual object based on a user force to a user input device may allow the user to more quickly and/or easily manipulate the pose of the virtual object with minimal movement (or no movement) of the user input device. It may also prevent a disconnect between the user input device and an instrument controlled by the user input device once the user exits a virtual object manipulation mode and resumes using the user input device to control an instrument.

Figure 1:
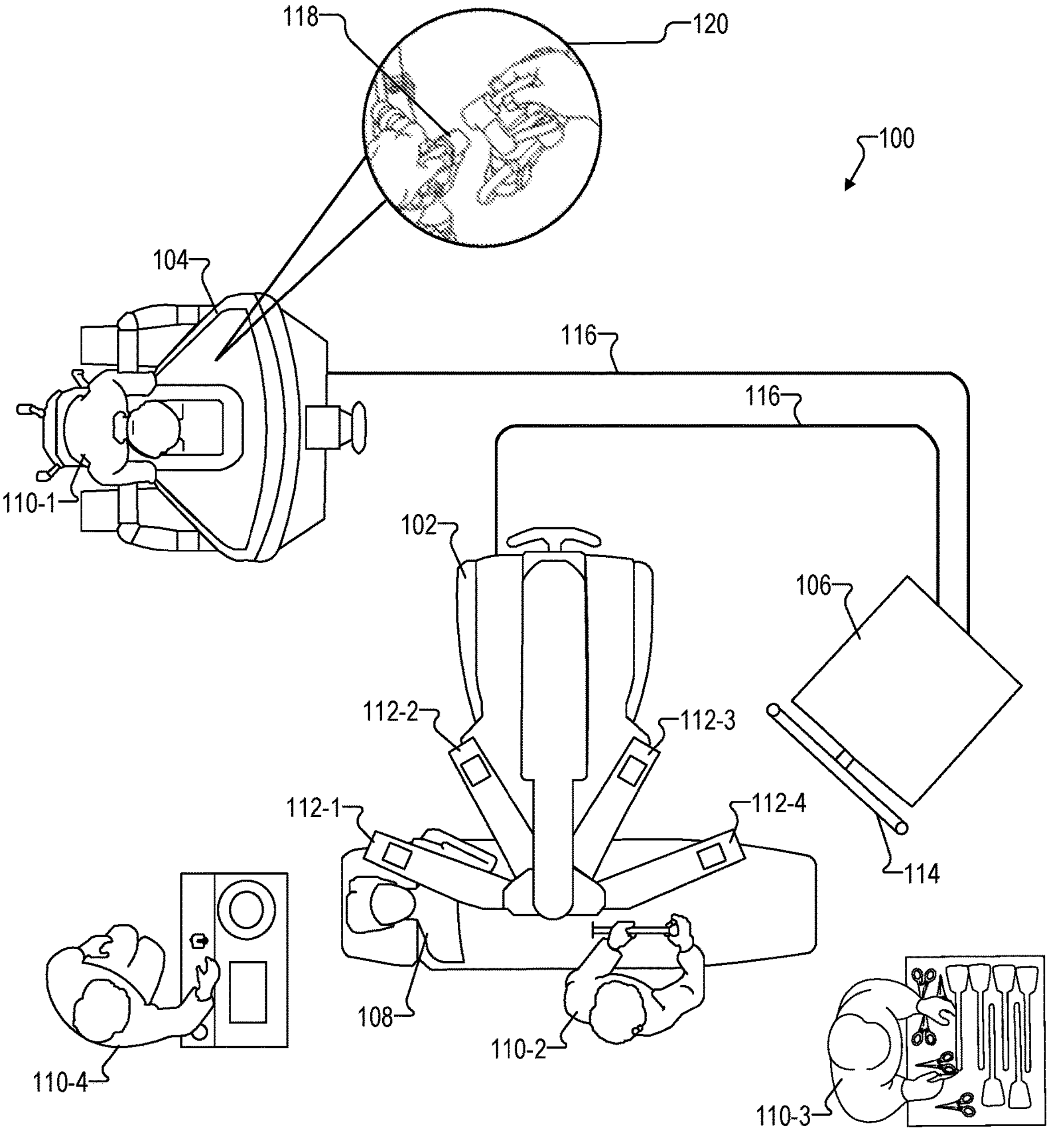
FIG. 1 shows an illustrative computer-assisted medical system.

FIG. 1 shows an illustrative computer-assisted medical system 100 that may be used to perform various types of medical procedures including surgical and/or non-surgical procedures.

As shown, computer-assisted medical system 100 may include a manipulator assembly 102 (a manipulator cart is shown in FIG. 1), a user control apparatus 104, and an auxiliary apparatus 106, all of which are communicatively coupled to each other. Computer-assisted medical system 100 may be utilized by a medical team to perform a computer-assisted medical procedure or other similar operation on a body of a patient 108 or on any other body as may serve a particular implementation. As shown, the medical team may include a first user 110-1 (such as a surgeon for a surgical procedure), a second user 110-2 (such as a patient-side assistant), a third user 110-3 (such as another assistant, a nurse, a trainee, etc.), and a fourth user 110-4 (such as an anesthesiologist for a surgical procedure), all of whom may be collectively referred to as users 110, and each of whom may control, interact with, or otherwise be a user of computer-assisted medical system 100. More, fewer, or alternative users may be present during a medical procedure as may serve a particular implementation. For example, team composition for different medical procedures, or for non-medical procedures, may differ and include users with different roles.

While FIG. 1 illustrates an ongoing minimally invasive medical procedure such as a minimally invasive surgical procedure, it will be understood that computer-assisted medical system 100 may similarly be used to perform open medical procedures or other types of operations. For example, operations such as exploratory imaging operations, mock medical procedures used for training purposes, and/or other operations may also be performed.

As shown in FIG. 1, manipulator assembly 102 may include one or more manipulator arms 112 (e.g., manipulator arms 112-1 through 112-4) to which one or more instruments may be coupled. The instruments may be used for a computer-assisted medical procedure on patient 108 (e.g., in a surgical example, by being at least partially inserted into patient 108 and manipulated within patient 108). While manipulator assembly 102 is depicted and described herein as including four manipulator arms 112, it will be recognized that manipulator assembly 102 may include a single manipulator arm 112 or any other number of manipulator arms as may serve a particular implementation. While the example of FIG. 1 illustrates manipulator arms 112 as being robotic manipulator arms, it will be understood that, in some examples, one or more instruments may be partially or entirely manually controlled, such as by being handheld and controlled manually by a person. For instance, these partially or entirely manually controlled instruments may be used in conjunction with, or as an alternative to, computer-assisted instrumentation that is coupled to manipulator arms 112 shown in FIG. 1.

During the medical operation, user control apparatus 104 may be configured to facilitate teleoperational control by user 110-1 of manipulator arms 112 and instruments attached to manipulator arms 112. To this end, user control apparatus 104 may provide user 110-1 with imagery of an operational area associated with patient 108 as captured by an imaging device. To facilitate control of instruments, user control apparatus 104 may include a set of master controls 118 (shown in close-up view 120). These master controls 118 may be manipulated by user 110-1 to control movement of the manipulator arms 112 or any instruments coupled to manipulator arms 112. For example, master controls 118 may be configured to detect a wide variety of hand, wrist, and finger movements by user 110-1. Manipulator arms 112 or any instruments coupled to manipulator arms 112 may mimic the dexterity of the hand, wrist, and fingers of user 110-1 across multiple degrees of freedom of motion. In this manner, user 110-1 may intuitively perform a procedure using one or more of manipulator arms 112 or any instruments coupled to manipulator arms 112. in order to perform one or more surgical procedures (e.g., an incision procedure, a suturing procedure, etc.).

Auxiliary apparatus 106 may include one or more computing devices configured to perform auxiliary functions in support of the medical procedure, such as providing insufflation, electrocautery energy, illumination or other energy for imaging devices, image processing, or coordinating components of computer-assisted medical system 100. In some examples, auxiliary apparatus 106 may be configured with a display monitor 114 configured to display one or more user interfaces, or graphical or textual information in support of the medical procedure. In some instances, display monitor 114 may be implemented by a touchscreen display and provide user input functionality. Augmented content provided by a region-based augmentation system may be similar, or differ from, content associated with display monitor 114 or one or more display devices in the operation area (not shown).

Manipulator assembly 102, user control apparatus 104, and auxiliary apparatus 106 may be communicatively coupled one to another in any suitable manner. For example, as shown in FIG. 1, manipulator assembly 102, user control apparatus 104, and auxiliary apparatus 106 may be communicatively coupled by way of control lines 116, which may represent any wired or wireless communication link as may serve a particular implementation. To this end, manipulator assembly 102, user control apparatus 104, and auxiliary apparatus 106 may each include one or more wired or wireless communication interfaces, such as one or more local area network interfaces, Wi-Fi network interfaces, cellular interfaces, and so forth.

Figure 2:
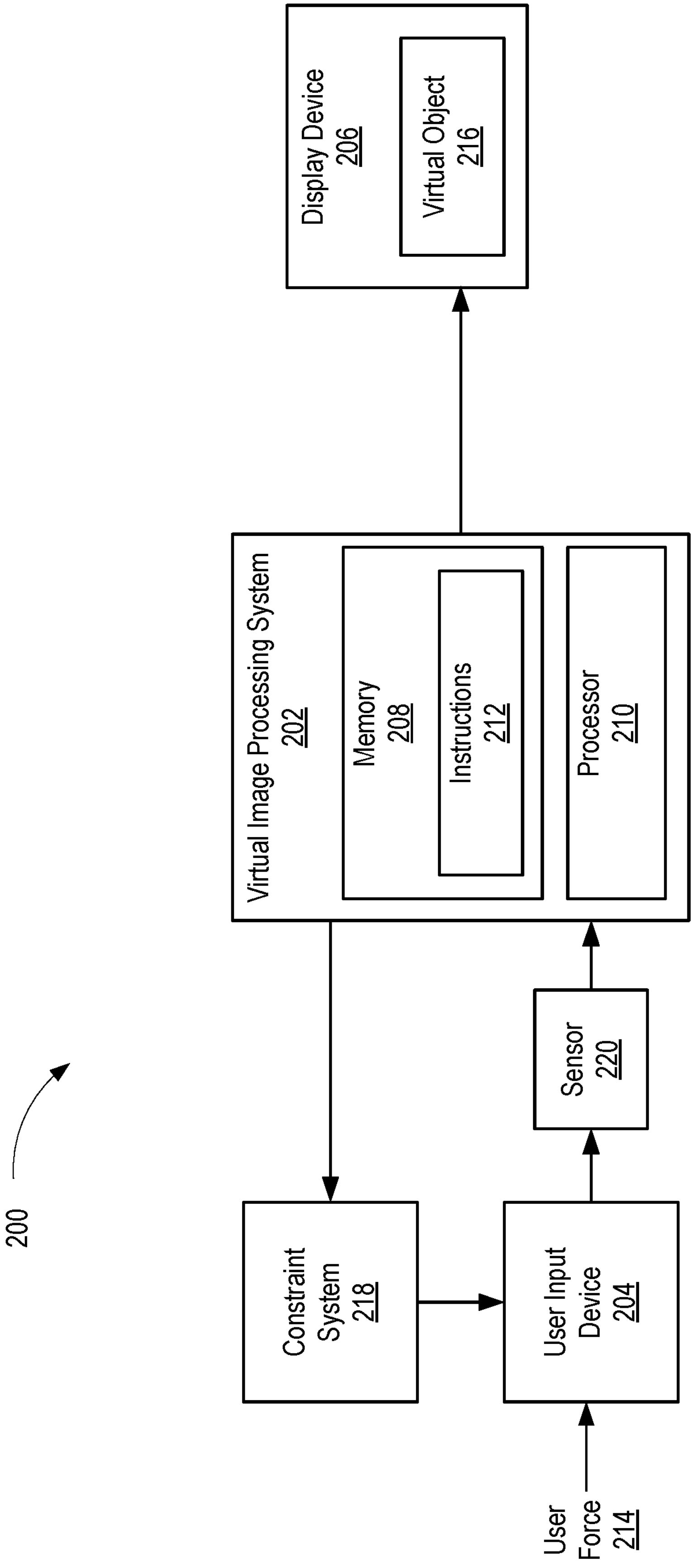
FIG. 2 shows an illustrative implementation including a virtual image processing system that may be incorporated into the computer-assisted medical system of FIG. 1.

FIG. 2 shows an illustrative implementation 200 configured to manipulate a pose of a virtual object being displayed during a medical procedure based on a user force that a user applies to a user input device. As shown, implementation 200 includes a virtual image processing system 202 in communication with a user input device 204 and a display device 206. Implementation 200 may include additional or alternative components as may serve a particular implementation. In some examples, implementation 200 or certain components of implementation 200 may be implemented by a computer-assisted medical system, such as computer-assisted medical system 100 discussed above.

Virtual image processing system 202 may be implemented by one or more computing devices and/or computer resources (e.g., processors, memory devices, storage devices, etc.) as may serve a particular implementation. As shown, virtual image processing system 202 may include, without limitation, a memory 208 and a processor 210 selectively and communicatively coupled to one another. Memory 208 and processor 210 may each include or be implemented by computer hardware that is configured to store and/or process computer software. Various other components of computer hardware and/or software not explicitly shown in FIG. 2 may also be included within virtual image processing system 202. In some examples, memory 208 and/or processor 210 may be distributed between multiple devices and/or multiple locations as may serve a particular implementation.

Memory 208 may store and/or otherwise maintain executable data used by processor 210 to perform any of the functionality described herein. For example, memory 208 may store instructions 212 that may be executed by processor 210. Memory 208 may be implemented by one or more memory or storage devices, including any memory or storage devices described herein, that are configured to store data in a transitory or non-transitory manner. Instructions 212 may be executed by processor 210 to cause virtual image processing system 202 to perform any of the functionality described herein. Instructions 212 may be implemented by any suitable application, software, code, and/or other executable data instance. Additionally, memory 208 may also maintain any other data accessed, managed, used, and/or transmitted by processor 210 in a particular implementation.

Processor 210 may be implemented by one or more computer processing devices, including general purpose processors (e.g., central processing units (CPUs), graphics processing units (GPUs), microprocessors, etc.), special purpose processors (e.g., application specific integrated circuits (ASICs), field-programmable gate arrays (FPGAs), etc.), image signal processors, or the like. Using processor 210 (e.g., when processor 210 is directed to perform operations represented by instructions 212 stored in memory 208), virtual image processing system 202 may perform various operations as described herein.

User input device 204 may be implemented by master controls 118 or other suitable device (e.g., a joystick, a button, a knob, a mouse, etc.) configured to be controlled by a user (e.g., user 110-1). User input device 204 may be movable by the user along one or more degrees of freedom of motion. For example, user input device 204 may be movable along one or more translational degrees of freedom (e.g., translatable along an x-axis of user input device 204, a y-axis of user input device 204, a z-axis of user input device 204, and/or combinations thereof) to allow the user to translate user input device 204 toward or away, side to side, and/or up or down relative to the user. Additionally or alternatively, user input device 204 may be movable about one or more rotational degrees of freedom (e.g., rotatable about an x-axis of user input device 204, a y-axis of user input device 204, a z-axis of user input device 204, and/or combinations thereof) to allow the user to rotate user input device 204 in a roll, pitch, and/or yaw direction. In some implementations, user input device 204 may further include one or more grips that may be movable in a degree of freedom relative to each other to allow the one or more grips to be squeezed and/or released.

Display device 206 may be implemented by monitor 114 or other suitable device configured to display a virtual object 216. Virtual object 216 may include any 3D model of an object. In some implementations, virtual object 216 may include a 3D model based on preoperative imagery of a body on or within which the medical procedure is being performed (e.g., a body of a live animal, a human or animal cadaver, a portion of human or animal anatomy, tissue removed from human or animal anatomies, non-tissue work pieces, training models, etc.). For example, virtual object 216 may include a 3D model of an anatomical object (e.g., an organ, soft tissue, connective tissue, etc.).

In some implementations, display device 206 may display virtual object 216 in combination with an image of a scene as captured by imaging device (e.g., an endoscope) during a medical procedure. In some examples, the scene may include a surgical area associated with a body on or within which the medical procedure is being performed (e.g., a body of a live animal, a human or animal cadaver, a portion of human or animal anatomy, tissue removed from human or animal anatomies, non-tissue work pieces, training models, etc.). In some instances, it may be desirable to manipulate the pose of virtual object 216 relative to the scene, such as to align virtual object 216 with the image captured by the imaging device.

Virtual image processing system 202 may be configured to manipulate the pose of virtual object 216 being displayed by display device 206 based on a user force 214 that a user applies to user input device 204, as described herein.

For example, virtual image processing system 202 may be configured to constrain a degree of freedom associated with movement of user input device 204. In some implementations, virtual image processing system 202 may be in communication with a constraint system 218 coupled with user input device 204 that is configured to constrain one or more degrees of freedom of user input device 204. Constraint system 218 may include any suitable device (e.g., a motor, a brake, a spring, etc.) configured to resist movement of user input device 204 in the constrained degree of freedom. Additionally or alternatively, constraint system 218 may include one or more electrical components configured to electrically resist movement of user input device 204 in the constrained degree of freedom. However, constraint system 218 is merely optional and other suitable configurations for constraining a degree of freedom associated with movement of user input device 204 may be used. For example, virtual image processing system 202 may directly constrain a degree of freedom associated with movement of user input device 204.

Virtual image processing system 202 may be configured to detect user force 214 applied to user input device 204 in the constrained degree of freedom. As shown in FIG. 2, virtual image processing system 202 may be in communication with a sensor 220 (e.g., a strain gauge, a transducer, a load cell, etc.) configured to directly measure user force 214 at user input device 204.

In some other implementations, sensor 220 may be configured to indirectly measure user force 214 at user input device 204. For example, sensor 220 may be configured to detect a small amount of movement (e.g., by an encoder, a linear variable differential transformer (LVDT), a piezo-electric transducer, etc.) of user input device 204 in response to user force 214 such that virtual image processing system 202 may be configured to determine an amount of user force 214 based on the detected movement. Alternatively, virtual image processing system 202 may be configured to receive a signal generated by sensor 220 (e.g., based on movement of user input device 204) as a proxy for user force 214. However, sensor 220 is merely optional and other suitable configurations for detecting user force 214 applied to user input device 204 in the constrained degree of freedom may be used.

In some implementations, virtual image processing system 202 may be configured to electrically detect user force 214 applied to user input device 204 in the constrained degree of freedom. For example, in instances where a motor is used to resist movement of user input device 204, the motor may generate an electrical current based on minimal movement of user input device 204. Virtual image processing system 202 may be configured to determine an amount of user force 214 based on the detected electrical current.

Virtual image processing system 202 may be configured to manipulate, based on user force 214, the pose of virtual object 216 being displayed by display device 206. For example, the pose of virtual object 216 may be manipulated by translating virtual object 216 in the display, rotating virtual object 216 in the display, adjusting a zoom of virtual object 216 in the display, and/or combinations thereof. In some implementations, the manipulation of the pose of virtual object 216 may mimic user force 214 applied to user input device 204. For example, virtual object 216 may be translated when user force 214 is applied in a translational degree of freedom and/or virtual object 216 may be rotated when user force 214 is applied in a rotational degree of freedom. In some implementations, the pose of virtual object 216 may be adjusted in a direction of an axis that is determined by an axis that user force 214 is applied to user input device 204 (e.g., if a user applies a rotational user force 214 to user input device 204 about an x-axis of user input device 204, virtual object 216 may be rotated about an x-axis of virtual object 216). Additionally or alternatively, a user may select a point or axis to manipulate virtual object 216 about the selected point or axis.

Virtual image processing system 202 may manipulate the pose of virtual object 216 when user force 214 is detected. For example, virtual image processing system 202 may continuously manipulate the pose of virtual object 216 as a user continuously applies user force 214 to user input device 204. Additionally or alternatively, virtual image processing system 202 may pulse the manipulation of the pose of virtual object 216 as a user pulses user force 214 to user input device 204.

In some implementations, the manipulation of the pose of virtual object 216 may be variable based on the detected user force 214. For example, virtual image processing system 202 may increase a speed of manipulation of the pose of virtual object 216 as user force 214 applied to user input device 204 increases and/or virtual image processing system 202 may decrease a speed of manipulation of the pose of virtual object 216 as user force 214 applied to user input device 204 decreases. Additionally or alternatively, the manipulation of the pose of virtual object 216 may be substantially constant based on the detected user force 214. For example, virtual image processing system 202 may manipulate the pose of virtual object 216 at a substantially constant speed while a user force 214 is detected. Still other suitable configurations for manipulating, based on user force 214, the pose of virtual object 216 being displayed by display device 206 may be used. For example, manipulation of the pose of virtual object 216 may be linearly and/or non-linearly scaled relative to user force 214, which may allow a smaller user force 214 to control larger virtual object 216 manipulations.

Figure 3:
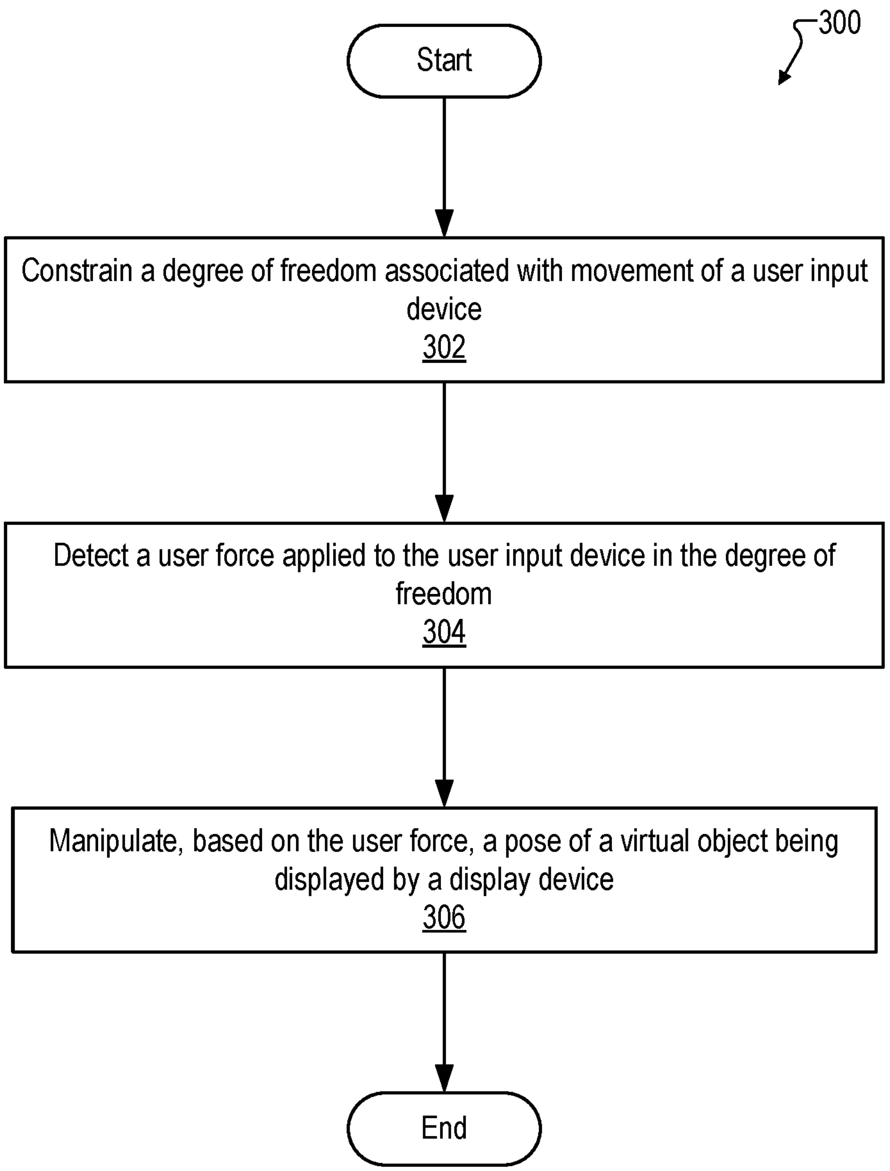
FIG. 3 shows an illustrative method of operating the virtual image processing system of FIG. 2.

FIG. 3 shows an illustrative method 300 that may be performed by virtual image processing system 202. While FIG. 3 illustrates exemplary operations according to one embodiment, other embodiments may omit, add to, reorder, and/or modify any of the operations shown in FIG. 3. Moreover, each of the operations depicted in FIG. 3 may be performed in any of the ways described herein.

As shown, virtual image processing system 202 may, at operation 302, constrain a degree of freedom associated with movement of user input device 204. Virtual image processing system 202 may, at operation 304, detect user force 214 applied to user input device 204 in the degree of freedom. Virtual image processing system 202 may, at operation 306, manipulate, based on user force 214, the pose of virtual object 216 being displayed by display device 206.

Figure 4A:
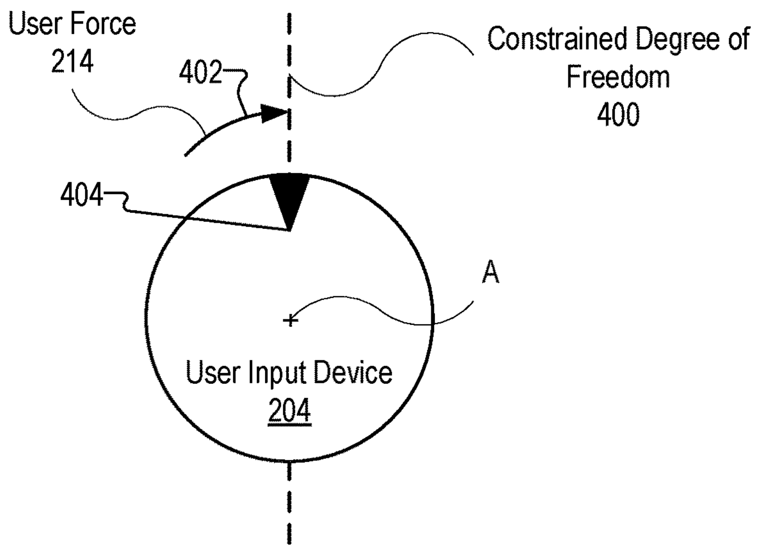
FIG. 4A shows an illustrative implementation of constraining a degree of freedom of the method of FIG. 3.

As an illustrative example, FIG. 4A shows user input device 204 constrained, by virtual image processing system 202, in a rotational degree of freedom 400 associated with rotation of user input device 204 in a clockwise direction (e.g., in the direction of arrow 402) oriented about axis A. Accordingly, if user force 214 is applied by a user to user input device 204 in the clockwise direction about axis A, the constrained degree of freedom 400 may resist movement of user input device 204 in the clockwise direction. This may cause user input device 204 to remain substantially static while user force 214 is applied to user input device 204, as shown by a reference point 404 on user input device 204. Virtual image processing system 202 may further detect user force 214 being applied to user input device 204 in the clockwise direction about axis A.

Figure 4B:
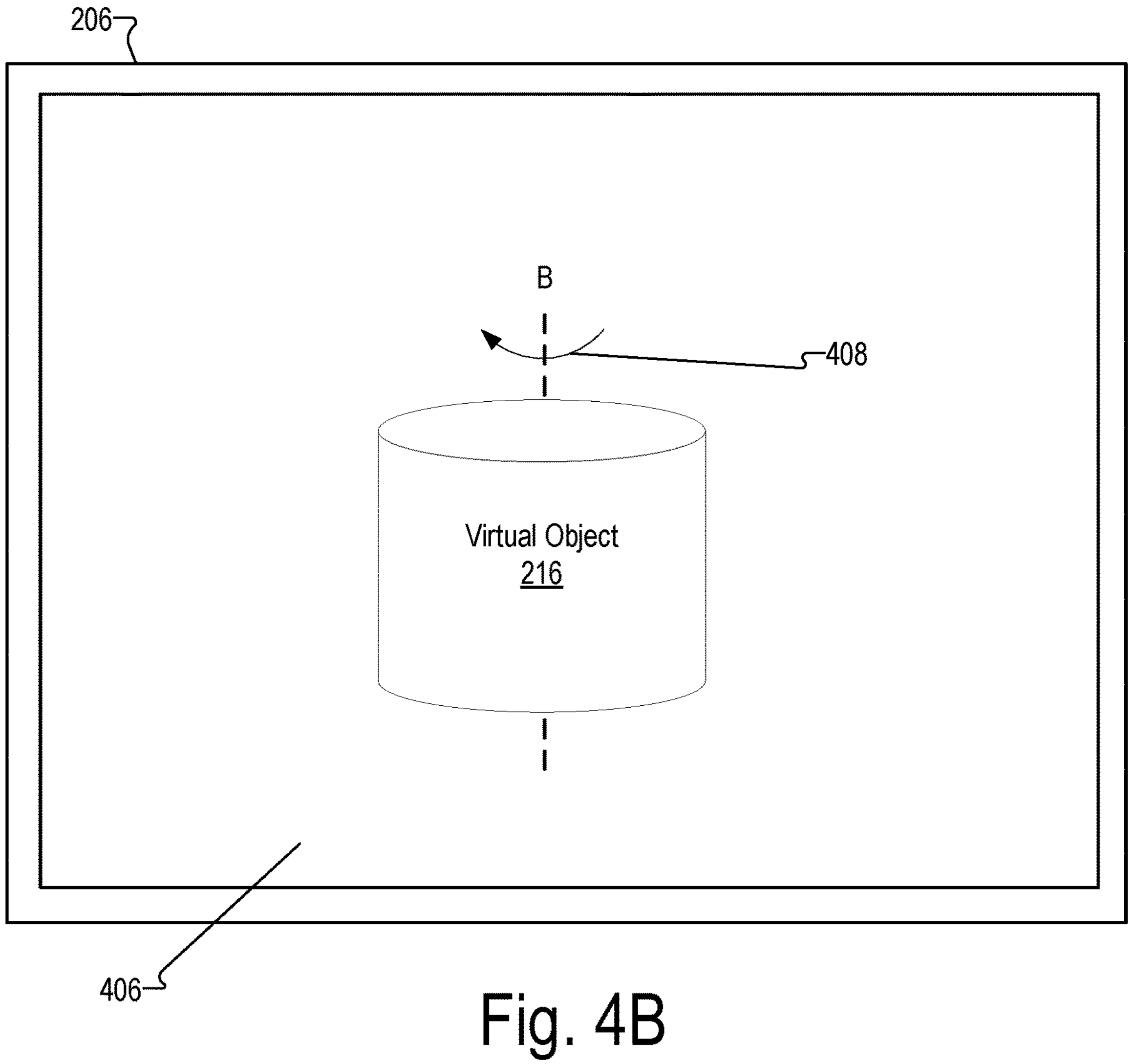
FIG. 4B shows an illustrative implementation of manipulating a pose of a virtual object of the method of FIG. 3.

FIG. 4B shows an illustrative example of manipulating, by virtual image processing system 202, the pose of virtual object 216 being displayed within an image 406 of display device 206 based on user force 214 detected by virtual image processing system 202. For example, virtual image processing system 202 may manipulate the pose of virtual object 216 within image 406 in a clockwise direction (e.g., in the direction of arrow 408) based on the detection of user force 214 applied to user input device 204 in the clockwise direction. Virtual image processing system 202 may further rotate virtual object 216 about an axis B of virtual object 216 that corresponds to the detection of user force 214 applied to user input device 204 about axis A of user input device 204.

Figure 5:
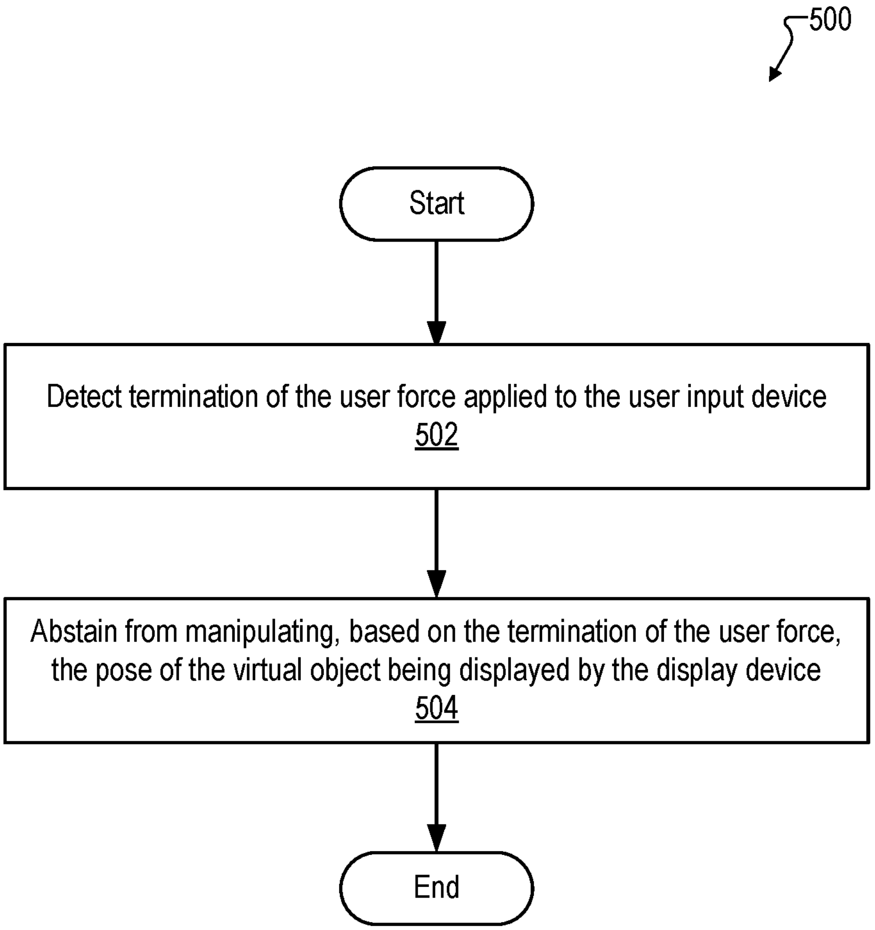
FIG. 5 shows another illustrative method of operating the virtual image processing system of FIG. 2.

FIG. 5 shows another illustrative method 500 that may be performed by virtual image processing system 202. While FIG. 5 illustrates exemplary operations according to one embodiment, other embodiments may omit, add to, reorder, and/or modify any of the operations shown in FIG. 5. Moreover, each of the operations depicted in FIG. 5 may be performed in any of the ways described herein.

As shown, virtual image processing system 202 may, at operation 502, detect a termination of user force 214 to user input device 204. For example, virtual image processing system 202 may directly, indirectly and/or electrically measure when a user stops applying user force 214 to user input device 204 (e.g., by sensor 220). Virtual image processing system 202 may, at operation 504, abstain from manipulating, based on the termination of user force 214, the pose of virtual object 216 being displayed by display device 206.

In some instances, it may be desirable to operate a computer-assisted medical system (e.g., computer-assisted medical system 100) in multiple modes. For example, the computer-assisted medical system may be operable in a virtual object manipulation mode in which user input device 204 is configured to be used to manipulate virtual objects 216. As another example, the computer-assisted medical system may be operable in an instrument manipulation mode in which user input device 204 is configured to be used to manipulate an instrument.

Figure 6:
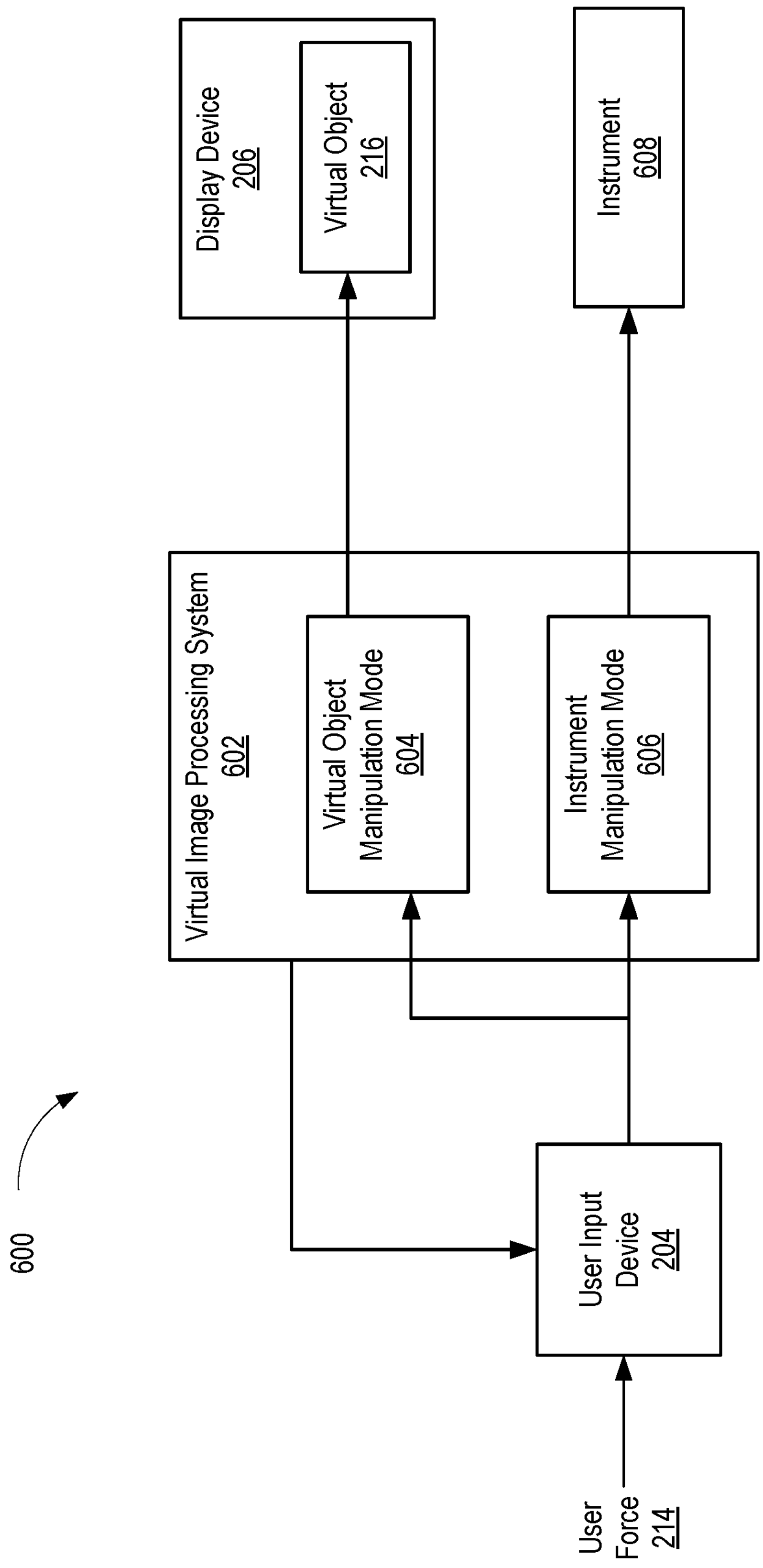
FIG. 6 shows another illustrative implementation including a virtual image processing system that may be incorporated into the computer-assisted medical system of FIG. 1.

Accordingly, FIG. 6 shows an illustrative implementation 600 including a virtual image processing system 602 that is operable in a virtual object manipulation mode 604 (e.g., while a computer-assisted medical system is in a virtual object manipulation mode) and an instrument manipulation mode 606 (e.g., while a computer-assisted medical system is in an instrument manipulation mode). Virtual image processing system 602 may implement or be similar to virtual image processing system 202. As shown, virtual image processing system 602 is in communication with user input device 204, display device 206, and one or more instruments 608 (e.g., an instrument attached to manipulator arms 112). Implementation 600 may include additional or alternative components as may serve a particular implementation. In some examples, implementation 600 or certain components of implementation 600 may be implemented by a computer-assisted medical system, such as computer-assisted medical system 100 discussed above.

In virtual object manipulation mode 604, virtual image processing system 602 may be configured to constrain a degree of freedom associated with movement of user input device 204, detect user force 214 applied to user input device 204 in the degree of freedom, and manipulate the pose of virtual object 216 being displayed by display device 206 based on the detected user force 214.

In instrument manipulation mode 606, virtual image processing system 602 may be configured to manipulate a pose of instrument 608 based on movement of user input device 204. In this mode, virtual image processing system 602 may be configured to abstain from constraining a degree of freedom associated with movement of user input device 204 such that user input device 204 is freely movable for manipulating instrument 608.

In some implementations, virtual image processing system 602 may be configured to abstain from manipulating the pose of instrument 608 while virtual image processing system 602 is in virtual object manipulation mode 604. For example, user input device 204 may be configured to manipulate movement of an imaging device (e.g., an endoscope) such that if user input device 204 is constrained, the position of the imaging device may also be constrained. Additionally or alternatively, virtual image processing system 602 may be configured to abstain from manipulating the pose of virtual object 216 while virtual image processing system 602 is in instrument manipulation mode 606.

Figure 7:
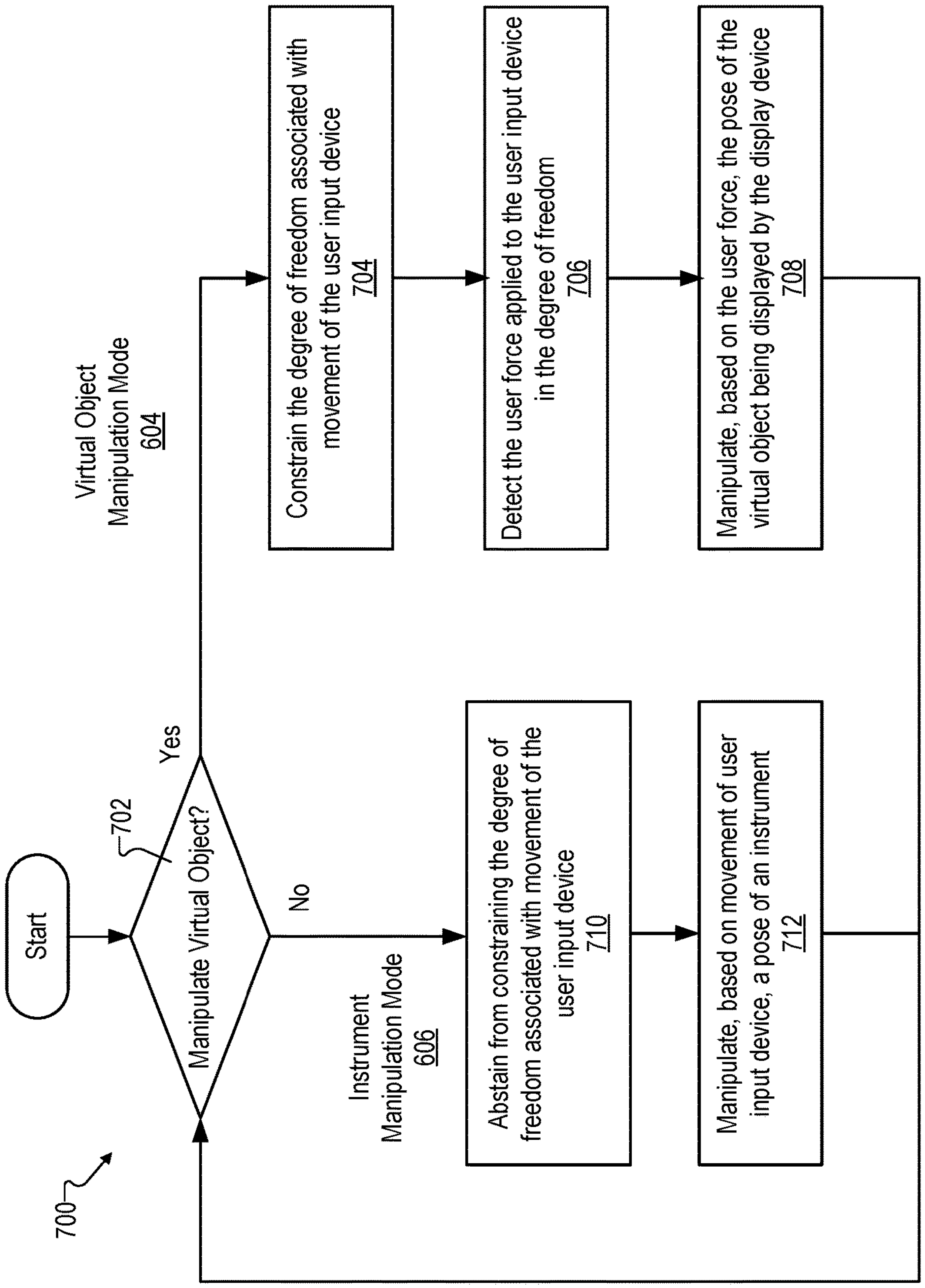
FIG. 7 shows an illustrative method of operating the virtual image processing system of FIG. 6.

FIG. 7 shows an illustrative method 700 that may be performed by virtual image processing system 602. While FIG. 7 illustrates exemplary operations according to one embodiment, other embodiments may omit, add to, reorder, and/or modify any of the operations shown in FIG. 7. Moreover, each of the operations depicted in FIG. 7 may be performed in any of the ways described herein.

As shown, virtual image processing system 602 may, at decision 702, be selected to manipulate a virtual object in virtual object manipulation mode 604. If virtual object manipulation mode 604 is selected (yes, decision 702), virtual image processing system 602 may, at operation 704, constrain a degree of freedom associated with movement of user input device 204. Virtual image processing system 602 may, at operation 706, detect user force 214 applied to user input device 204 in the degree of freedom. Virtual image processing system 602 may, at operation 708, manipulate, based on user force 214, the pose of virtual object 216 being displayed by display device 206.

If virtual object manipulation mode 604 is not selected (no, decision 702), virtual image processing system 602 may be operated in instrument manipulation mode 606. In this mode, virtual image processing system 602 may, at operation 710, abstain from constraining the degree of freedom associated with movement of user input device 204. Virtual image processing system 602 may at operation 712, manipulate, based on movement of user input device 204, a pose of instrument 608. In some implementations, a user may transition virtual image processing system 602 between virtual object manipulation mode 604 and/or instrument manipulation mode 606.

In some instances, it may be desirable to provide fine control of the pose of virtual object 216. For example, relatively small movements of user input device 204 may be mapped with corresponding movements of the pose of virtual object 216.

Figure 8:
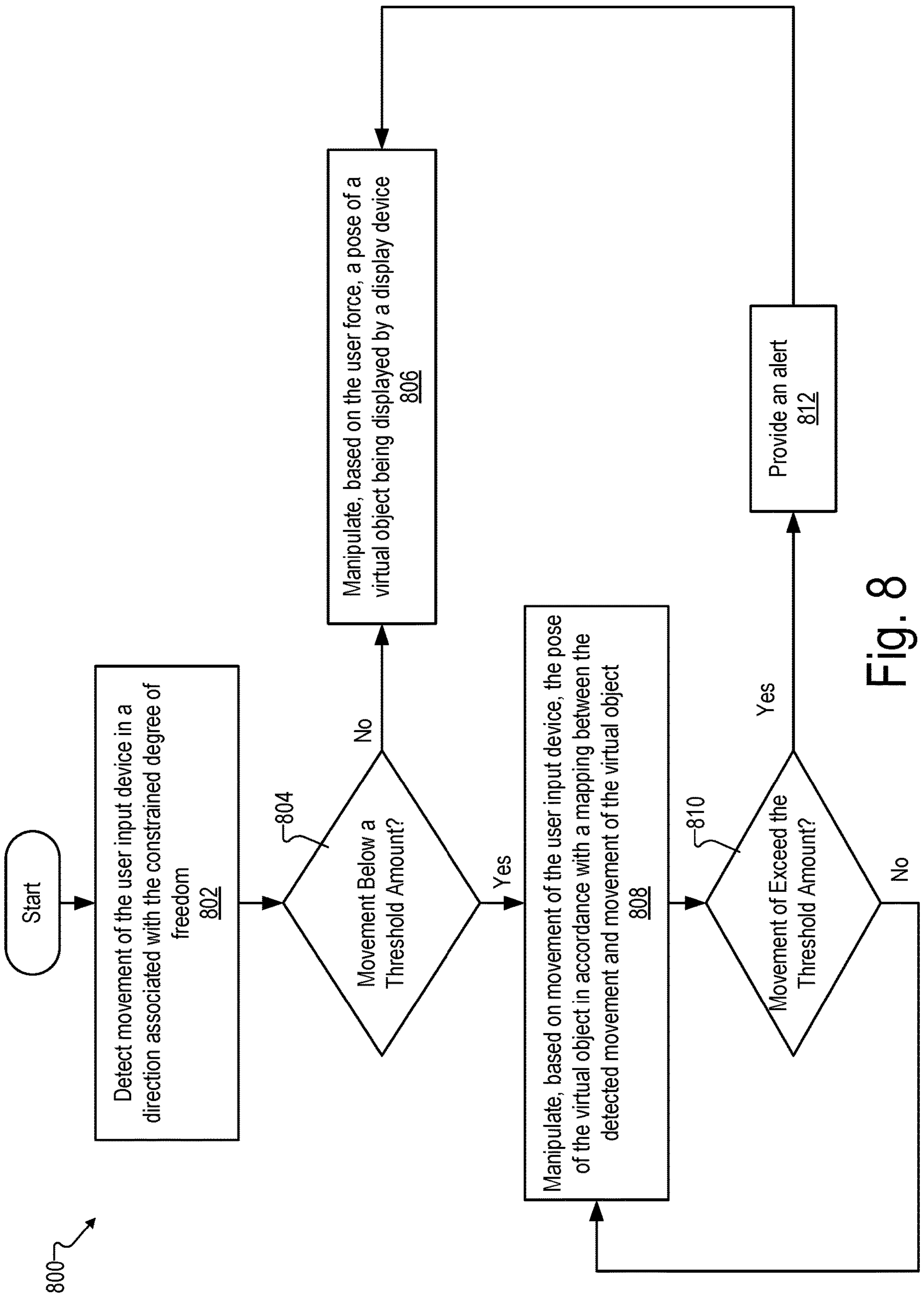
FIG. 8 shows another illustrative method of operating the virtual image processing system of FIG. 6.

Accordingly, FIG. 8 shows another illustrative method 800 that may be performed by virtual image processing system 602 while virtual image processing system 602 is in virtual object manipulation mode 604. While FIG. 8 illustrates exemplary operations according to one embodiment, other embodiments may omit, add to, reorder, and/or modify any of the operations shown in FIG. 8. Moreover, each of the operations depicted in FIG. 8 may be performed in any of the ways described herein.

As shown, virtual image processing system 602 may, at operation 802, detect movement of user input device 204 in a direction associated with the constrained degree of freedom. Virtual image processing system 602 may, at decision 804, determine whether the detected movement of user input device 204 is below a threshold amount (e.g., a select angle of rotation). If the detected movement is above the threshold amount (no, decision 804), virtual image processing system 602 may, at operation 806, manipulate, based on user force 214, the pose of virtual object 216 being displayed by display device 206. If the detected movement is below the threshold amount (yes, decision 804), virtual image processing system 602 may, at operation 808, manipulate, based on movement of user input device 204, the pose of virtual object 216 in accordance with a mapping between the detected movement and movement of virtual object 216.

In this mapping configuration, virtual image processing system 602 may, at decision 810, determine whether the detected movement of user input device 204 exceeds the threshold amount. If the detected movement does not exceed the threshold amount (no, decision 810), virtual image processing system 602 may further manipulate the pose of virtual object 216 based on movement of user input device 204 in accordance with a mapping between the detected movement and movement of virtual object 216 (operation 808). If the detected movement does exceed the threshold amount (yes, decision 810), virtual image processing system 602 may resume manipulating, based on user force 214, the pose of virtual object 216 being displayed by display device 206 (operation 806). In some implementations, virtual image processing system 602 may, at operation 812, provide an alert (e.g., haptic feedback, audio alert, visual alert, etc.) when the threshold amount is exceeded. Still other suitable configurations for manipulation virtual object 216 may be used.

For example, virtual image processing system 602 may decouple rotational movement and translational movement of user input device 204 for mapping rotational movement of user input device 204 with rotational movement of virtual object 216 and/or mapping translational movement of user input device 204 with translational movement of virtual object 216. In some implementations, mapping of rotational movement of virtual object 216 may be decoupled from mapping of translational movement of virtual object 216. For example, rotational movement of virtual object 216 may be mapped to movement of user input device 204 and translational movement of virtual object 216 may be mapped to user force 214, or vice versa.

Figure 9:
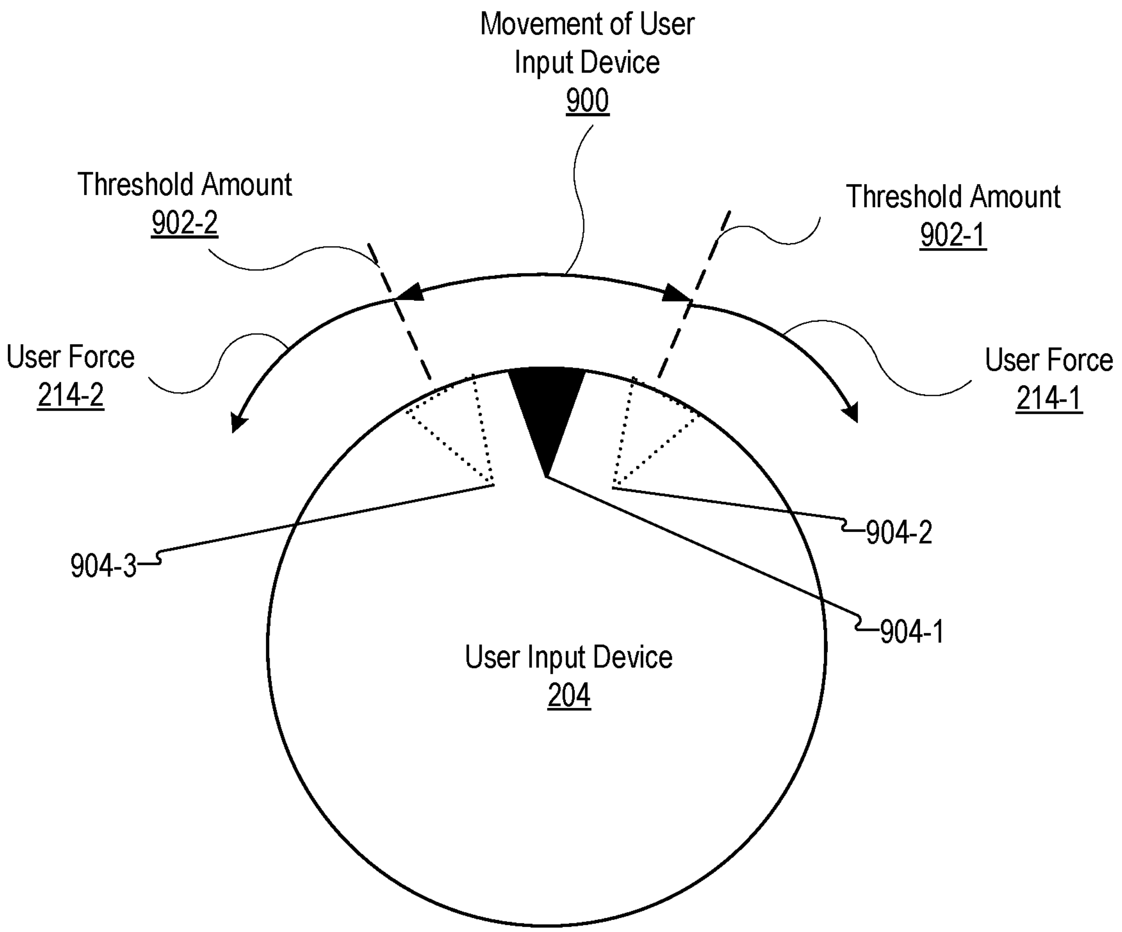
FIG. 9 shows an illustrative implementation of constraining a degree of freedom of a user input device of the implementation of FIG. 6.

As an illustrative example, FIG. 9 shows user input device 204 constrained, by virtual image processing system 602, in a rotational degree of freedom that may allow movement (e.g., in the direction of arrow 900) of user input device 204 below a threshold amount 902 (e.g., threshold amount 902-1 to 902-2). For example, virtual image processing system 602 may constrain a degree of freedom of user input device 204 in a clockwise and/or counterclockwise direction to allow rotational movement of user input device 204 below threshold amount 902 in the clockwise and/or counterclockwise direction. As shown in the illustrated example, a user may rotate user input device 204 from an initial position, indicated by a first reference point 904-1, in the clockwise direction to threshold amount 902-1, indicated by a second reference point 904-2, and/or in the counterclockwise direction to threshold amount 902-2, indicated by a third reference point 904-3. The movement of user input device 204 below threshold amount 902 may manipulate the pose of virtual object 216 in accordance with mapping between the detected movement of user input device 204 and movement of virtual object 216.

When movement 900 of user input device 204 exceeds threshold amount 902 in the clockwise and/or counterclockwise direction, the constrained degree of freedom associated with movement of user input device 204 may prevent movement of user input device 204 beyond threshold amount 902. This may allow a user to exert user force 214 to user input device 204. For example, user force 214-1 may be applied to user input device 204 when movement of user input device 204 exceeds threshold amount 902-1 in the clockwise direction and/or user force 214-2 may be applied to user input device 204 when movement of user input device 204 exceeds threshold amount 902-2 in the counterclockwise direction. In this configuration, the pose of virtual object 216 may be manipulated based on user force 214.

Figure 10:
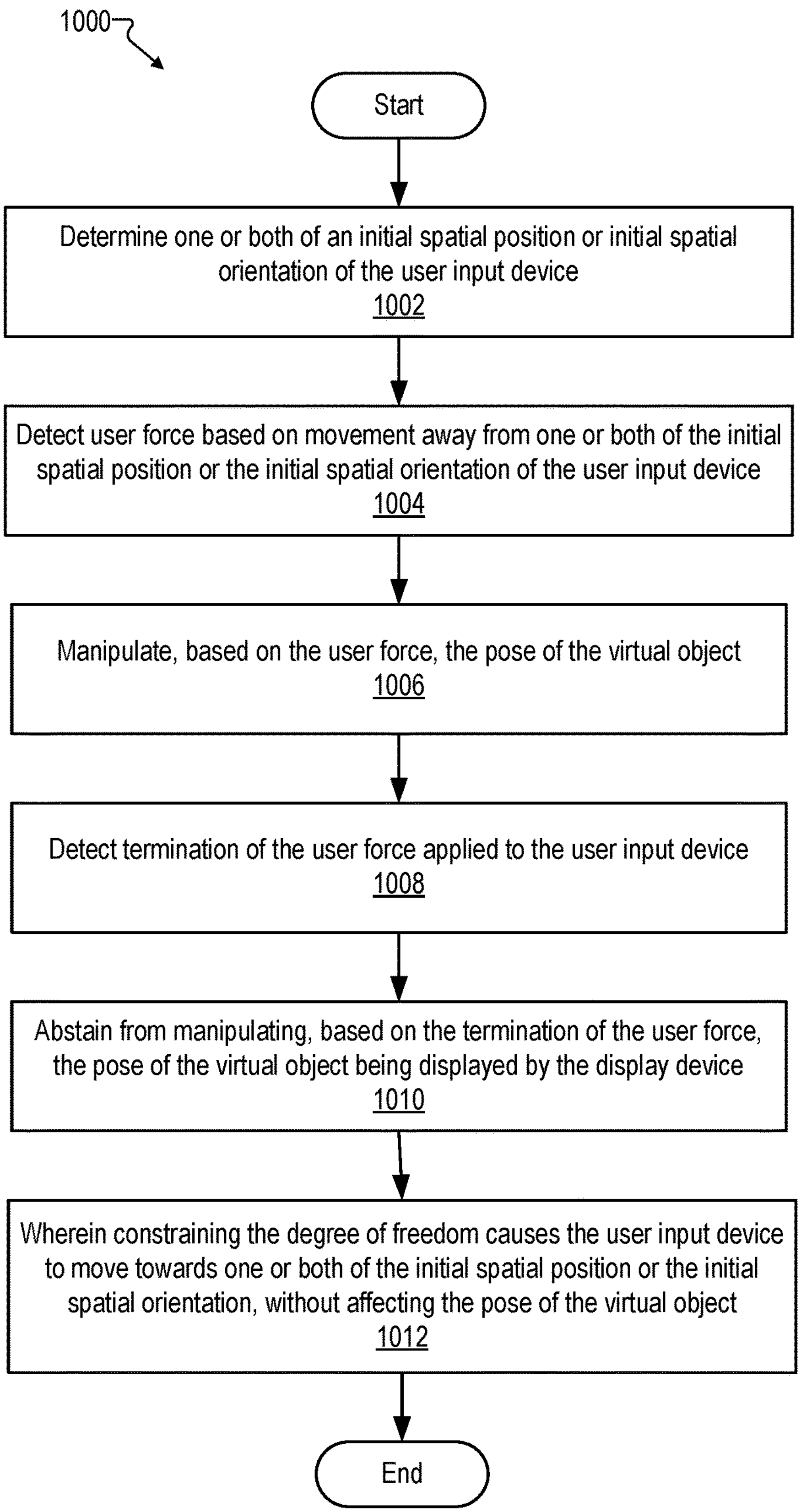
FIG. 10 shows an illustrative method of operating another implementation including a virtual image processing system that may be incorporated into the computer-assisted medical system of FIG. 1.

FIG. 10 shows another illustrative method 1000 that may be performed by virtual image processing system 602 with limited movement of user input device 204 (e.g., below a threshold amount). While FIG. 10 illustrates exemplary operations according to one embodiment, other embodiments may omit, add to, reorder, and/or modify any of the operations shown in FIG. 10. Moreover, each of the operations depicted in FIG. 10 may be performed in any of the ways described herein.

As shown, virtual image processing system 602 may, at operation 1002, determine one or both of an initial spatial position (e.g., a translational position) or initial spatial orientation (e.g., a rotational position) of user input device 204. Such an initial spatial position and/or initial spatial orientation may be determined as the spatial position and/or spatial orientation of user input device 204 when virtual image processing system 602 is transitioned from instrument manipulation mode 606 to virtual object manipulation mode 604. Virtual image processing system 602 may, at operation 1004, detect user force 214 based on movement away from one or both of the initial spatial position or the initial spatial orientation of user input device 204. Virtual image processing system 602 may, at operation 1006, manipulate the pose of virtual object 216 based on user force 214.

Virtual image processing system 602 may, at operation 1008, detect termination of user force 214 applied to user input device 204. Virtual image processing system 602, may at operation 1010, abstain from manipulating, based on the termination of user force 214, the pose of virtual object being displayed by display device 206. Virtual image processing system 602 may, at operation 1012, cause user input device 204, with the constrained degree of freedom, to move towards one or both of the initial spatial position or the initial spatial orientation without affecting the pose of virtual object 216. For example, a displacement of user input device 204 from the initial spatial position and/or initial spatial orientation may invoke virtual image processing system 602 (e.g., by a proportional-derivative controller, a spring-damper system, etc.) to generate a force to move user input device 204 back towards the initial spatial position and/or initial spatial orientation. This may allow the spatial position and/or spatial orientation of user input device 204 to correspond to a pose of the instrument when virtual image processing system 602 is transition from virtual object manipulation mode 604 to instrument manipulation mode 606.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 11:
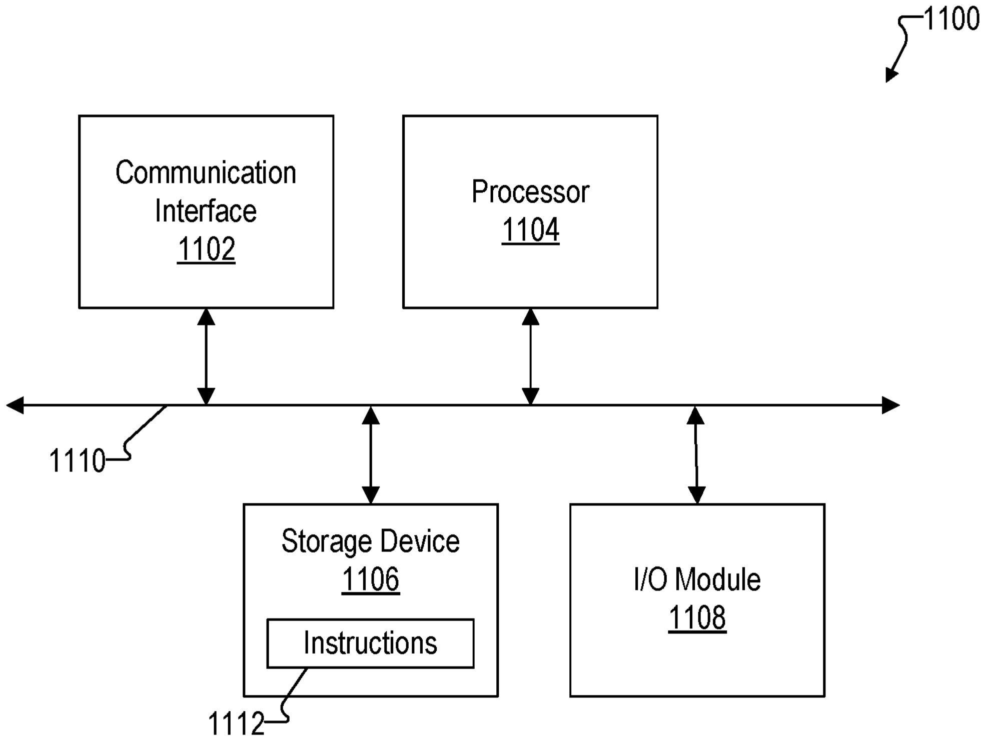
FIG. 11 shows an illustrative computing system according to principles described herein.

FIG. 11 shows an illustrative computing device 1100 that may be specifically configured to perform one or more of the processes described herein. Any of the systems, computing devices, and/or other components described herein may be implemented by computing device 1100.

As shown in FIG. 11, computing device 1100 may include a communication interface 1102, a processor 1104, a storage device 1106, and an input/output ("I/O") module 1108 communicatively connected one to another via a communication infrastructure 1110. While an illustrative computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data and/or interpreting, executing, and/or directing execution of one or more of the instructions, processes, and/or operations described herein. Processor 1104 may perform operations by executing computer-executable instructions 1112 (e.g., an application, software, code, and/or other executable data instance) stored in storage device 1106.

Storage device 1106 may include one or more data storage media, devices, or configurations and may employ any type, form, and combination of data storage media and/or device. For example, storage device 1106 may include, but is not limited to, any combination of the non-volatile media and/or volatile media described herein. Electronic data, including data described herein, may be temporarily and/or permanently stored in storage device 1106. For example, data representative of computer-executable instructions 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
constrain a degree of freedom associated with movement of a user input device;
detect a user force applied to the user input device in the degree of freedom; and
manipulate, based on the user force, a pose of a virtual three-dimensional (3D) model relative to a scene depicted within an image captured by an imaging device and being displayed by a display device.

2. The system of claim 1, wherein the processor is further configured to execute the instructions to:
detect a termination of the user force to the user input device; and
abstain from manipulating, based on the termination of the user force, the pose of the virtual 3D model being displayed by the display device.

3. The system of claim 1, wherein the processor is further configured to execute the instructions to constrain the degree of freedom associated with movement of the user input device while a computer-assisted medical system is in a virtual object manipulation mode in which the user input device is configured to be used to manipulate virtual 3D models.

4. The system of claim 3, wherein the processor is further configured to execute the instructions to abstain from manipulating a pose of an instrument while the computer-assisted medical system is in the virtual object manipulation mode.

5. The system of claim 3, wherein the processor is further configured to execute the instructions to manipulate, based on movement of the user input device, a pose of an instrument based on the computer-assisted medical system transitioning from the virtual object manipulation mode to an instrument manipulation mode in which the user input device is configured to be used to manipulate instruments.

6. The system of claim 5, wherein the processor is further configured to execute the instructions to abstain from constraining the degree of freedom associated with movement of the user input device while the computer-assisted medical system is in the instrument manipulation mode.

7. The system of claim 5, wherein the processor is further configured to execute the instructions to abstain from manipulating the pose of the virtual 3D model while the computer-assisted medical system is in the instrument manipulation mode.

8. The system of claim 1, wherein the processor is further configured to execute the instructions to:
detect a movement of the user input device below a threshold amount in the degree of freedom; and
further manipulate, based on the movement, the pose of the virtual 3D model in accordance with a mapping between the movement and movement of the virtual 3D model.

9. The system of claim 8, wherein the processor is further configured to execute the instructions to:
detect that the movement of the user input device exceeds the threshold amount; and resume manipulating the pose of the virtual 3D model based on the user force instead of the movement of the user input device.

10. The system of claim 9, wherein the processor is further configured to execute the instructions to provide an alert when the movement of the user input device exceeds the threshold amount.

11. The system of claim 1, wherein the manipulating the pose of the virtual 3D model includes one or more of rotating the virtual 3D model about an axis of the virtual 3D model, translating the virtual 3D model within the image being displayed by the display device, or adjusting a zoom of the virtual 3D model within the image being displayed by the display device.

12. The system of claim 1, wherein the processor is further configured to execute the instructions to increase a speed of manipulation of the pose of the virtual 3D model as the user force applied to the user input device increases.

13. The system of claim 1, wherein the processor is further configured to execute the instructions to decrease a speed of the manipulation of the pose of the virtual 3D model as the user force applied to the user input device decreases.

14. The system of claim 1, wherein detecting the user force applied to the user input device is based on movement of the user input device away from one or both of an initial spatial position or an initial spatial orientation of the user input device.

15. The system of claim 14, wherein constraining the degree of freedom causes the user input device to move towards one or both of the initial spatial position or the initial spatial orientation, without affecting the pose of the virtual 3D model, when the user force is no longer being applied to the user input device.

16. The system of claim 14, wherein the processor is further configured to execute the instructions to:

determine the initial spatial position of the user input device based on a spatial position of the user input device when a computer-assisted medical system is transitioned from an instrument manipulation mode, in which the user input device is configured to be used to manipulate instruments, to a virtual object manipulation mode, in which the user input device is configured to be used to manipulate virtual 3D model; and determine the initial spatial orientation of the user input device based on a spatial orientation of the user input device when the computer-assisted medical system is transitioned from the instrument manipulation mode to the virtual object manipulation mode.

17. The system of claim 16, wherein the spatial position and the spatial orientation of the user input device corresponds to a pose of an instrument when the computer-assisted medical system is transitioned from the virtual object manipulation mode to the instrument manipulate mode.

18. A system comprising:

a user input device;

a display device configured to display a virtual three-dimensional (3D) model; and a control system communicatively coupled with the user input device and the display device, wherein the control system is configured to:

constrain a degree of freedom associated movement of the user input device, detect a user force applied to the user input device in the degree of freedom, and manipulate, based on the user force, a pose of the virtual 3D model relative to a scene depicted within an image captured by an imaging device and being displayed by the display device.

19. A method comprising:

constraining a degree of freedom associated with movement of a user input device;

detecting a user force applied to the user input device in the degree of freedom; and manipulating, based on the user force, a pose of a virtual three-dimensional (3D) model relative to a scene depicted within an image captured by an imaging device and being displayed by a display device.

20. The method of claim 19, further comprising:

detecting a termination of the user force applied to the user input device; and abstaining from manipulating, based on the termination of the user force, the pose of the virtual 3D model being displayed by the display device.

* * * * *